United States Patent [19]

Smith et al.

[11] Patent Number: 4,778,825
[45] Date of Patent: Oct. 18, 1988

[54] MACROPHAGE STIMULATION BY QUADROL

[75] Inventors: Daniel J. Smith, Stow; Sanjay R. Patel, Akron; Edwin C. Rowland, Athens, all of Ohio

[73] Assignee: The University of Akron, Akron, Ohio

[21] Appl. No.: 901,927

[22] Filed: Aug. 29, 1986

[51] Int. Cl.$^4$ ............................................. A61K 31/13
[52] U.S. Cl. ..................................................... 514/669
[58] Field of Search ......................................... 514/669

[56] References Cited

U.S. PATENT DOCUMENTS

| | | | |
|---|---|---|---|
| 2,697,113 | 12/1954 | Lundsted et al. | 260/584 |
| 4,035,480 | 7/1977 | Green et al. | 424/78 |
| 4,290,904 | 9/1981 | Poper et al. | 252/118 |
| 4,593,053 | 6/1986 | Jevne et al. | 523/111 |

FOREIGN PATENT DOCUMENTS 1147262  5/1983  Canada .
0023978  2/1981  European Pat. Off. .

OTHER PUBLICATIONS

Chemical Abstracts 94:214382n (1981).
Chemical Abstracts 95:205800u (1981).
Adams, D. O.; Johnson, W. J.; Marino, P. A.; and Dean, J. H.; Effect of Pyran Copolymer on Activation of Murine Macrophages: Evidence for Incomplete Activation by Use of Functional Markers, Cancer Res., 43:3633, 1983.
Allison, A. C.; Ferluga, J.; Prydy, H.; and Schorlemmer, H. U.; The Role of Macrophage Activation in Chronic Inflammation, Agent's Actions, 8: 27, 1978.
Bianco, C.; Eden, A.; and Cohn, Z. A.; The Induction of Macrophage Spreading: Role of Coagulation Factors and The Complement System, The Journal of Experimental Medicine, vol. 144, pp. 15-31-1544, 1976.
Dunn, P. A.; Eaton, W. R.; Lopatin, E. D.; McEntire, J. E. and Papermaster, B. W.; Limphokine-Stimulated Macrophage Phagocytosis of Fluorescent Microspheres: A Rapid New Assay, J. Immunol. Methods, 64: 71, 1983.
Garvey, J. S.; Cremer, N. E.; and Sussdorf, D. H.; Methods in Immunology, 3rd Ed. pp. 443-450, Addison-Wesley Publishing Company, Inc., 1977.
Gordon, S.; Unkeless, J. C.; and Cohn, Z. A.; Induction of Macrophage Plasminogen Activator by Endotoxin Stimulation and Phagocytosis., J. Exp. Med. 140: 995, 1974.
Hall, J. L.; Dean, W. E. and Pacoffsky, E. A.; J. Am. Chem. Soc., vol. 82, pp. 3303-1969.
Hoffman, W. W.; Korst, J. J.; Miblack, J. F.; and Cronin, T. H., N,N'-Diodadecyl-N', N'-bis(2-Hydroxyethyl)Propanediamine; Antiviral Activity and Interferon Stimulation in Mice, Antimicrobial Agents and Chemotherapy, vol. 3, pp. 498-502, 1973.
Kaplan, A. M.; Morahan, P. S.; and Regelson, W.; Induction of Macrophage-Mediated Tumor Cell Cytotoxicity by Pryan Copolymer, J. Natl. Canc. Inst., 52: 1919, 1974.
Leibovich, S. J.; and Danon, D.; Promotion of Wound Repair in Mice by Application of Glucan, J. of the Reticuloendothelial Society, vol. 27, pp. 1-11, 1980.
Levine, H. I.; Mark, E. H.; and Fiel, R. J.; Divalent Cation Binding Specificities and Macrosphere Formation of Pyran Copolymer and Related Polycarboxylates, Arch. Biochem. Biophys., 184:156, 1977.
Morahan, P. S. and Kaplan, A. M.; Macrophage Activation and Antitumor Activity of Biologic and Synthetic Agents, Int. J. Cancer 17: 82, 1976.
Morland, B. and Kaplan, G.; Macrophage Activation In Vivo and In Vitro, Exptl. Cell Res., 108: 279, 1977.
Najjar, V. A. and Fridkin, M.; Annals of N.Y. Acad. Sci., Antineoplastic, Immunogenic and Other Effects of the Tetrapeptide Tuftsin: "A Natural Activator of Phagocyte Cells: An Overview", vol. 419, Part 1, Retrospective, The N.Y. Acad. Sci., N.Y., 1983.
Onozaki, K.; Takenawa, T.; Homma, Y.; and Hashimoto, T.; The Mechanism of Macrophage Activation Induced by Ca$^{++}$ Ionophore, Cellular Immunol., 75:242, 1983.
Orama, M.; Saarinen, H.; and Kaila, L.; Formation of Copper (II), Cobalt (II), Zinc (II) and Lead (II) Complexes with N,N,N', N'-tetrakis(2-hydroxypropyl)ethylenediamine in Aqueous Solution, Finn. Chem. Lett. 1979:182, 1979.
Pike, L.; and Yoe, J. H.; Spectrophotometric Determination of Manganese with N,N,N'N'-tetrakis(2-hydroxypropyl)ethylenediamine, Anal. Chim. Acta, 31:318, 1964.
Vogtle, F.; Sieger, H.; and Muller, W. M.; Stoichiometric Alkali and Alkaline Earth Metal Complexes of Ethanolamine Compounds of Polypod (Octopus Molecule) Type I., J. Chem. Research(S), 398, 1978.
Wahl, S. M.; Wahl, L. M.; McCarthy, J. B.; Chedid, L.; and Mergenhagen, S. E.; Macrophage Activation by Mycobacterial Water-Soluble Compounds and Synthetic Muramyl Dipeptide, J. Immunology, 122: 2226, 1979.

Primary Examiner—Leonard Schenkman
Attorney, Agent, or Firm—Oldham & Oldham Co.

[57] ABSTRACT

Quadrol has been found to stimulate macrophage activity in warm blooded animals. As a consequence, Quadrol may be used to combat bacterial infection, remove degenerated tissue, and promote new tissue growth. Quadrol may be applied topically, e.g., as the active agent in a wound dressing.

5 Claims, No Drawings

MACROPHAGE STIMULATION BY QUADROL

TECHNICAL FIELD

This invention relates to methods and agents for stimulating macrophage activity in warm blooded animals, including man.

BACKGROUND ART

Macrophages, or large phagocytes, are important in wound healing, fighting infection and in a variety of immune responses in warm blooded animals including man. They promote the wound healing process in various ways. For example, macrophages engulf and destroy bacteria and degenerating tissue. They also kill intracellular pathogens. They also appear to secrete and release factors which promote the growth of new collagen. Macrophages are found in the blood stream and in various tissues including the liver and the peritoneium.

Macrophages can be specifically activated as a part of the cellular immune response by various materials including immune complexes, compliment components, lymphokines and tuftsin. Other macrophage stimulation agents include lipopolysaccharides (LPS), muramyl dipeptide, physiologic cation complexing agents such as certain pyran copolymers and other polycarboxylates, and certain ionphores.

Administration of a macrophage stimulating agent to a host animal increases the activity of macrophages in the host, so that they more effectively perform their various functions. These various functions are known in the art, and some of these functions have been described above. In particular, administration of a macrophage stimulating agent to a wound site in a host animal stimulates macrophages in the host so that they more effectively perform the various healing functions, some of which have been discussed above.

The majority of known macrophage stimulators are macromolecular in nature. Most of them are naturally occurring materials or derivitives of naturally occurring materials, and most are quite expensive. Pyran copolymers are among the few known synthetic macrophage stimulating agents.

Quadrol, N,N,N',N'-tetrakis(2-hydroxypropyl)ethlenediamine is a known compound having the structural formula (A)

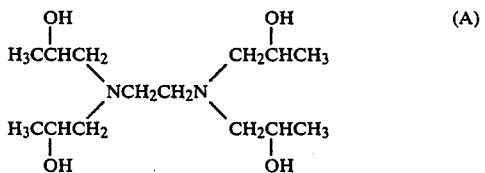

Quadrol can be synthesized by reacting 1 mole of ethlenediamine with 4 moles of propylene oxide, as described for example in U.S. Pat. No. 2,697,113 to Lundsted et al. Quadrol is known to a complex a number of polyvalent cations such as $Co^{2+}$, $Cu^{2+}$, and $Zn^{2+}$ and has been used as an analytical reagent for the determination of trivalent manganese ($Mn^{+++}$) in solution. Quadrol is often used as a cross-linking agent and catalyst in the synthesis of polyurethane foams and membranes. Quadrol has not been found previously to be useful for any biological purpose, as far as applicants are aware.

It is an object of this invention to provide an inexpensive and non-toxic agent having macrophage stimulation activity.

It is a further object of this invention to provide wound dressings which incorporate an inexpensive, non-toxic macrophage stimulating agent.

According to this invention, macrophage cell activity in a warm blooded animal is promoted by administering Quadrol to said animal.

BEST MODE FOR CARRYING OUT INVENTION

Applicants have discovered that Quadrol is biologically active. In particular, Quadrol has macrophage stimulating activity. In addition, Quadrol is virtually non-toxic.

Macrophage stimulating activity of Quadrol has been demonstrated in vitro and in vivo, using standard test methods, which will be described in greater detail in the examples. The stimulatory effect of Quadrol has been found to be both concentration and time dependent in both in vitro and in vivo experiments.

Quadrol may be administered topically to an animal in need of treatment for infection or other condition which responds to macrophage stimulation. Quadrol may be administered as a composition of matter comprising said Quadrol and a suitable pharmaceutically acceptable carrier, particularly a solid or semisolid (e.g., paste) carrier in which Quadrol is insoluble. When Quadrol is applied topically to a wound, lesion or sore in a warm blooded animal, including man, Quadrol stimulates the activity of macrophages at the site of the wound, lesion or sore. The macrophages, in turn, promote the healing proces, e.g. by englulfing and destroying bacteria and degenerating tissue, by promoting closure of the wound or lesion, and by promoting the growth of new tissue. Quadrol is potentially a particularly valuable agent for the treatment of wounds and sores which either do not heal or which heal very slowly when treated according to presently known methods. Wounds and sores heal very slowly in diabetics, for example, and Quadrol appears to be a potentially valuable agent for promoting the healing of wounds and sores in such patients.

According to a particularly preferred embodiment of this invention, a wound dressing containing Quadrol as the biologically active agent is prepared and applied to a skin wound or lesion of the host animal. The wound dressing may comprise a standard bandage material, e.g. gauze, impregnated with an aqueous solution of Quadrol having a concentration ranging from about 1 to about 40 millimolar (mM). All or a portion of the bandage material may be so impregnated. Preferably, however, a pharmaceutically effective amount of Quadrol is incorporated into an ointment, which in turn is applied to the portion of the bandage which is placed over the wound or lesion. The ointment base may be conventional and is preferably of paste consistency. The amount of Quadrol may be approximately 0.1 to 0.4 percent of the total ointment weight. The bandage is then applied to the skin wound or lesion in a conventional manner. Of course, when the bandage is only partially impregnated with Quadrol, the Quadrol-impregnated portion must be placed over the wound site.

While a conventional bandage material is the preferred support or carrier for topical administration, Quadrol may be absorbed on other pharmaceutically acceptable supports or carriers, a polymer membrane for example, and applied to a skin wound or lesion.

Quadrol-impregnated wound dressings according to this invention promotes the wound healing process in a variety of ways, as indicated above, by stimulating the macrophage cells of the host animal. In constrast, the presently known wound dressings merely protect the wound from infection and foreign matter and, when a therapeutically active agent is present, reduce infection by attacking bacteria without assisting the healing process in other ways, as for example by destruction and removal of dead or degenerating tissue, or by promoting the growth of new collagen.

For minor wounds, Quadrol may be applied topically in the form of a paste or ointment. Such paste or ointment may comprise Quadrol and other conventional pharmaceutically acceptable paste or ointment ingredients.

Compared to other known stimulators of macrophage spreading and phagocytosis, Quadrol is unusual in that it is synthetic, of low molecular weight, and inexpensive. The low cost is a major advantage, particularly in the case of intractable wound infections which require repeated administration over a period of a number of days.

This invention will now be described further with reference to the examples which follow. Example 1 shows that macrophage cells retain their viability at Quadrol concentrations far above those required for effective macrophage stimulation. Examples 2, 3, 4 and 6 represent standard in vitro tests (or minor modifications thereof) used to show macrophage stimulation activity. Example 5 shows that Quadrol is an effective macrophage stimulator in vivo; it also shows that Quadrol retains its activity when bonded to a solid support or carrier. This is important because Quadrol is water soluble, and can be effective over a much longer period of time in an insolubilized form.

EXAMPLE 1

Macrophage Cell Viability In Vitro

Six to eight week old mice were used as a source of resident peritoneal exudate cells. After asphyxiation of the mice by $CO_2$, the peritoneal cavity was washed with Alsever's solution. The cells were collected, washed three times with PBS (phosphate buffered saline solution, 0.01M, pH 7.2), and resuspended in Eagle's minimum essential medium (EMEM), pH 7.2, supplemented with 10 percent heat inactivated fetal bovine serum, 1 percent glutamine (200 mM), 100 units/mL penicillin, and 100 mg/L streptomycin (hereinafter "supplemented EMEM"), to a concentration of $2 \times 10^6$ cells/mL. This cell suspension (hereinafter "cell suspension") was used in all assays.

Quadrol solutions for testing in all examples were prepared as follows: Quadrol was dissolved in 10 mM phosphate bufferend saline solution (PBS) and adjusted to pH 7.1 with sodium hydroxide or hydrochloric acid to make 5 mM, 20 mM, 40 mM, 60 mM and 160 mM stock solutions. These stock solutions were diluted with supplemented EMEM to make 0.5 mM, 1 mM, 4 mM, 16 mM and 32 mM test solutions.

To assay macrophage viability after incubation with Quadrol, Leighton test tubes, containing either cell suspension ($2 \times 10^6$ cells/mL) (control) or a test suspension prepared by mixing 0.1 mL each of cell suspenson and one of the stock solutions of Quadrol described above, were incubated in a 37° C. in a humid environment containing 5 percent (by volume) $CO_2$ and having relative humidity of 100 percent. (This same composition was used throughout the examples wherever a humid environment is called for, and the term "$CO_2$-containing humid environment" when used hereafter denotes an environment of this composition). Incubation times were 1 hour, 2 hours, 4 hours, 6 hours and 24 hours. At each time interval, test tubes were removed from the incubator and 0.3 mL of the cell suspension was taken out of each test tube and placed in a small siliconized test tube. Trypan blue dye solution (0.1 mL) was added and mixed gently for 5 minutes to allow sufficient time for the dead cells to take up the dye. Slides of each cell suspension were prepared by layering a portion of the suspension onto a clean glass coverslip and examined with a light microscope and the number of live and dead cells was counted. Viability (in percentage terms) is calculated by dividing the number of live cells counted by the total number of cells counted, and multiplying by 100.

Results are shown in Table I. This table shows the percentage of viable cells for the control and for each Quadrol solution concentration tested at each incubation time tested. Results represent averages of 7 identical experiments.

TABLE I

| | Percentage of Viable Cells | | | | |
| --- | --- | --- | --- | --- | --- |
| | Incubation time, hours | | | | |
| | 0.5 | 1 | 2 | 4 | 6 |
| Quadrol concentration: | | | | | |
| 0.5 mM | 93 | 90 | 90 | 85 | — |
| 1 mM | 89 | 92 | 91 | 92 | 88 |
| 4 mM | 79 | 72 | 67 | — | 64 |
| 16 mM | 88 | 74 | 67 | 63 | 51 |
| Control: | 92 | 92 | 88 | 92 | 88 |

Results with 0.5 mM and 1 mM Quadrol showed no significant difference of the control in cell viability. Quadrol concentrations of 4 mM and 16 mM, on the other hand, significantly reduced cell viability; cell viability in cells incubated for 6 hours in a 16 mM Quadrol solution had only half the viability of cells incubated in the control medium for a similar length of time.

EXAMPLE 2

Macrophage Spreading In Vitro

Samples of cell suspension (0.100 mL each) were layered on to clean glass coverslips (#2, Corning Glass Co.) and incubated for 30 minutes at 37° C. in a $CO_2$-containing humid environment. After incubation the coverslips were washed to remove nonadherent cells, then covered with 0.1 mL of either a Quadrol test solution, LPS (lipopolysaccharide serotype, buffered to pH 7.2) 20 mg/L or supplemented EMEM (control). All solutions and suspensions applied to coverslips were adjusted to a pH of about 7.1–7.2 to avoid acid induced spreading. incubation times were 1 hour, 2 hours, 4 hours, 6 hours and 24 hours. At the end of each incubation period, the coverslips were washed with warm PBS and fixed by the addition of 2 percent glutaraldehyde, pH 7.2, prewarmed to 37° C. After 5 minutes, the coverslips were washed with 0.1M sodium cacodylate buffer and examined under a Zeiss phase contrast microscope at 400× magnification. Both normal and spread cells were counted. Spread cells appeared gray and had an extended apron on diameter, whereas the unspread (normal) cells were rounded and refractile. Approximately 400 cells were counted per coverslip. Seven experiments were carried out for each concentration and incubation time tested.

Table II below shows the effect of Quadrol on macrophage spreading as a function of incubation time and concentration. In Table II below, "% Spreading" indicates the percentage of cells which had spread.

TABLE II

| | % Spreading Time, Hours | | | | |
|---|---|---|---|---|---|
| Solution | 1 | 2 | 4 | 6 | 24 |
| Quadrol: | | | | | |
| 1 mM | 22 | 45 | 88 | 92 | 93 |
| 4 mM | 22 | 34 | 81 | 70 | 69 |
| 16 mM | 10 | 15 | 60 | 41 | 40 |
| LPS | 31 | 37 | 67 | 67 | 69 |
| Control | 20 | 26 | 28 | 30 | 35 |

As shown in Table II, the increase in macrophage spreading was linear with time with a maximum achieved at 4 hours for all solutions tested (except the 1 mM Quadrol solution and the control, where slight further increases in spreading after 4 hours were noted). After 4 hours, concentrations of 1 mM and 4 mM Quadrol produced enhanced spreading of 88 percent and 80 percent, respectively, as compared to 28 percent in the control. In fact, spreading values exceeded those obtained with LPS, which is a known macrophage stimulating agent. Quadrol concentrations at 16 mM showed less stimulatory effect than either LPS or the 1 mM, 4 mM Quadrol solutions; however, this is not of practical interest since data in Example 1 show that Quadrol at 16 mM concentration has an adverse effect on cell viability. Consequently, use of Quadrol in lower concentrations is indicated.

EXAMPLE 3

Bead Phagocytosis by Macrohages In Vitro Effect of Dosage

The degree of macrophage phagocytosis in this example is an indication of the extent of macrophage stimulation activity. A greater percentage of phagocytosis indicates a greater stimulation of macrophage activity. The bead phagocytosis assay for resident peritoneal macrophages described in this example was modified from Dunn et al, "Limphokine-Stimulated Macrophage Phagocytosis of Fluorescent Microspheres: A Rapid New Assay", *J. Immunol. Methods*, 64:71, 1983."

Solutions tested in this example were Quadrol (1.0 mM and 4.0 mM) (prepared as described in Example 1), tuftsin (tuftsin acetate, 0.01 mg/L of supplemented EMEM), LPS (prepared as described in Example 2), and supplemented EMEM, (control). Doses of tuftsin and LPS used in this example are known to be stimulatory.

Cell suspensions (75 μL each) were layered onto clean coverslips and incubated for 60 minutes at 37° in a $CO_2$-containing humid environment. After washing with PBS buffer, 25 μL of solution to be tested and 25 μL of a suspension of polystyrene beads 3 μin diameter, in supplemented EMEM (2.25 × 10⁷ beads/mL medium) were added to each coverslip. Following incubation for 45 minutes at 37° in a $CO_2$-containing humid environment, the coverslips were washed with PBS, fixed using 2 percent glutaraldehyde, and stored in 0.1M sodium cacodylate buffer. Five replicate coverslips were used for each solution tested in each experiment. Wet mounts of the coverslips were prepared and observed under a Zeiss phase contrast microscope at 400× to 1000×. Cells with 2 or more beads within the outline of the cell membrane and in the same focal plane were considered as phagocytizing cells. Approximately 300–400 cells per coverslip were observed. The percentage phagocytosis was determined by counting both phagocytizing and non-phagocytizing cells, and dividing the former by the total and multiplying by 100.

Results are shown in Table III

TABLE III

| Solution | Phagocytosis (%) |
|---|---|
| Quadrol: | |
| 1 mM | 41 |
| 4 mM | 57 |
| Tuftsin | 53 |
| LPS | 64 |
| Control | 34 |

Results in Table III represent mean values obtained in five identical experiments for each solution tested. The standard error in each case is about plus or minus 4 percent.

Results in this example show that Quadrol in either 1 or 4 mM concentration has a macrophage stimulating effect. The effect of 4 mM Quadrol exceeds that of Tuftsin, a known macrophage stimulating agent tested at a known stimulatory concentration.

EXAMPLE 4

Bead Phagocytosis by Macrophages In Vitro Effect of Time

Solutions tested in this example were Quadrol (4 mM), LPS and control (supplemented EMEM).

The procedure of Example 3 was followed, except that the test solutions were those indicated in the preceeding paragraph and the incubation times of the test solutions and bead suspensions were 5 minutes, 15 minutes, 30 minutes and 45 minutes.

TABLE IV

| | Incubation Time (Min.) | | | |
|---|---|---|---|---|
| Solution | 5 | 15 | 30 | 45 |
| Quadrol (4 mM) | 63 | 70 | 71 | 68 |
| LPS | 60 | 68 | 76 | 63 |
| Control | 4 | 47 | 55 | 48 |

Each value shown in Table IV represents the mean of five identical experiments. The standard error in each case is in the range of plus or minus 2 to 3 percent.

Data in Table IV show that stimulation of macrophage phagocytic activity reached a peak at 30 minutes and thereafter declined. Data also show that there were no significant differences in the activity of Quadrol (4 mM) and LPS at any incubation time tesed and that both exhibited far greater phagocytosis than did the control.

EXAMPLE 5

Macrophage Stimulation In Vivo

Balb/c mice 6 to 8 weeks old (3 per group) were injected intraperitoneally with 0.2 mL of a suspension of PBS containing 35 mg glass beads with Quadrol covalently attached, 35 mg glass beads alone or PBS alone.

The glass beads as purchased were microporous beads (pore diameter 50 nM; purchased from Pierce Chemical Co.) having a long chain alkyl amine bonded thereto. Quadrol was bonded to the beads by first swelling the beads in toluene, then treating them with diphenylmethane diisocyanate (MDI) in toluene under conditions such that only one isocyanate group reacted with the amine group, then further treating the beads with Quadrol in the presence of a catalyst under conditions such that only one hydroxyl group of the Quadrol reacted with the isocyanate group to form the desired covalent linkage. Finally, the beads were soaked in methanol for 24 hours and oven dried under vacuum.

Three days after injection, the mice were sacrificed and their peritoneal exudate cells obtained as described in Example 1. These cells were then placed on coverslips for determination of spreading. (The criteria for determining the percent of cell spreading are described in Example 2). After 1 hour of incubation at 37° C., the coverslips were washed, fixed with glutaraldehyde and examined microscopically. The precentage of spreading of macrophage cells on each coverslip is indicated in Table V below.

TABLE V

| Mice Injected With: | % Spreading |
|---|---|
| Quadrol on glass beads | 43.1 |
| Glass beads | 18.2 |
| PBS | 14.6 |

This example shows that Quadrol retains its macrophage stimulating activity even when bonded to a solid support. It also shows that Quadrol is effective in vivo.

EXAMPLE 6

Glucose Utilization

Six to eight weeks old balb/c female mice were used as the source of peritoneal exudate cells. The mice were injected with sterile thioglycollate (1.5 mL). Four days later, the mice were asphyxiated and the cells harvested and washed with PBS as described in Example 1.

Peritoneal cells were suspended in supplemented EMEM containing N-2-hydroxyethylpiperazine-N'-2-ethanesulfonic acid (HEPES)(25 mM). (The composition of supplemented EMEM is described in Example 1). Portions of the cell suspension (0.2 mL each) were placed in flat bottomed, 96-well plates (Corning No. 25860) and incubated for 2 hours at 37° C. in a $CO_2$ containing-humid atmosphere. Non-adherent cells were removed by washing with EMEM. Test suspensions were prepared by mixing equal volumes of the cell suspension described in this example with Quadrol 1 mM and Quadrol 4 mM stock solutions prepared as described in Example 1. The cell suspension described earlier in this example (with no added Quadrol) served as the control. Each of the resulting suspensions was incubated for 24, 48 and 72 hours and the percentage of glucose remaining in each suspension at each time interval was measured using a Sigma #5-10 glucose kit. The amount of glucose remaining is reported in Table VI. Also reported in Table VI is the percentage of uptake enhancement, which is calculated as shown below:

(1) % Uptake-100- % Remaining
(2) % Enhancement=

$$\frac{\% \text{ Uptake in Test}}{\% \text{ Uptake in Control}} - 100$$

TABLE VI

| | % Glucose Remaining and % Uptake Enhancement | | | | | |
|---|---|---|---|---|---|---|
| | % Glucose Remaining Time, Hrs. | | | % Uptake Enhancement Time, Hrs. | | |
| Quadrol Concentration | 24 | 48 | 72 | 24 | 48 | 72 |
| 1 mM | 78 | 57 | 42 | 22 | 34 | 16 |
| 4 mM | 71 | 41 | 28 | 61 | 84 | 44 |
| Control | 82 | 68 | 50 | 0 | 0 | 0 |

The above results show that utilization, or uptake of glucose, is enhanced considerably by a 4 mM Quadrol test suspension, and much less so by a 1 mM Quadrol test suspension.

While in accordance with the patent statutes, a preferred embodiment and best mode has been presented, the scope of the invention is not limited thereto, but rather is measured by the scope of the attached claims.

What is claimed is:

1. A method of promoting healing of a wound in a warm blooded animal by stimulating macrophage cell activity at the wound site, which comprises applying a composition comprising a pharmaceutically effective amount of Quadrol and a pharmaceutically acceptable carrier to said wound site.

2. A method according to claim 1 in which Quadrol is applied topically to a wound or the skin of said animal.

3. A method according to claim 2 in which said Quadrol is contained in an ointment.

4. A method according to claim 2 in which said Quadrol is contained in a wound dressing.

5. A wound dressing comprising an absorbent bandage having applied thereto a composition comprising Quadrol and a pharmaceutically acceptable carrier.

* * * * *